US010656007B2

(12) United States Patent
Akkaraju et al.

(10) Patent No.: US 10,656,007 B2
(45) Date of Patent: May 19, 2020

(54) ASYMMETRICAL ULTRASOUND TRANSDUCER ARRAY

(71) Applicant: EXO IMAGING INC., Oakland, CA (US)

(72) Inventors: Sandeep Akkaraju, Wellesley, MA (US); Haesung Kwon, Austin, TX (US); Brian Bircumshaw, Oakland, CA (US)

(73) Assignee: EXO IMAGING INC., Redwood City, CA (US)

( * ) Notice: Subject to any disclaimer, the term of this patent is extended or adjusted under 35 U.S.C. 154(b) by 0 days.

(21) Appl. No.: 15/951,118

(22) Filed: Apr. 11, 2018

(65) Prior Publication Data

US 2019/0316957 A1   Oct. 17, 2019

(51) Int. Cl.
| | | |
|---|---|---|
| *G01H 11/08* | (2006.01) | |
| *H01L 41/18* | (2006.01) | |
| *G01N 29/07* | (2006.01) | |
| *G01S 15/02* | (2006.01) | |
| *H01L 41/113* | (2006.01) | |
| *B81B 3/00* | (2006.01) | |

(52) U.S. Cl.
CPC ............ *G01H 11/08* (2013.01); *G01N 29/07* (2013.01); *G01S 15/02* (2013.01); *H01L 41/1132* (2013.01); *H01L 41/183* (2013.01); *B81B 3/0021* (2013.01)

(58) Field of Classification Search
CPC ....... G01H 11/08; G01S 15/02; H01L 41/183; H01L 41/1132; G01N 29/07; B81B 3/0021
See application file for complete search history.

(56) References Cited

U.S. PATENT DOCUMENTS

| | | |
|---|---|---|
| 2007/0103697 A1 | 5/2007 | Degertekin |
| 2012/0289897 A1 | 11/2012 | Friend et al. |
| 2013/0293065 A1 | 11/2013 | Hajati et al. |
| 2019/0176193 A1* | 6/2019 | Shulepov ............. A61B 8/4483 |

FOREIGN PATENT DOCUMENTS

WO          2017216139 A1     12/2017

* cited by examiner

*Primary Examiner* — Nam D Pham
(74) *Attorney, Agent, or Firm* — Wilson Sonsini Goodrich & Rosati (57) ABSTRACT

An array of micromachined ultrasonic transducers (MUTs). The array has first and second rows, the MUTs in the first row being equally spaced by a horizontal pitch in a horizontal direction, the MUTs in the second row being equally spaced by the horizontal pitch in the horizontal direction. The MUTs in the second row are shifted along the horizontal direction by a first horizontal distance relative to the MUTs in the first row and shifted along a vertical direction by a first vertical distance relative to the MUTs in the first row. The first horizontal distance is greater than zero and less than the horizontal pitch. The first vertical distance ranges from one tenth of a horizontal width of a MUT to a half of a vertical height of a MUT.

25 Claims, 11 Drawing Sheets

ASYMMETRICAL ULTRASOUND TRANSDUCER ARRAY

BACKGROUND

A. Technical Field

The present invention relates to imaging devices, and more particularly, to imaging devices having micromachined ultrasound transducers (MUTs).

B. Background of the Invention

A non-intrusive imaging system for imaging internal organs of a human body and displaying images of the internal organs transmits signals into the human body and receives signals reflected from the organ. Typically, transducers that are used in an imaging system are referred to as transceivers and some of the transceivers are based on photo-acoustic or ultrasonic effects. In general, transceivers are used for imaging as well as other applications, such as medical imaging, flow measurements in pipes, speaker, microphone, lithotripsy, heating tissue for therapeutics, and highly intensive focused ultrasound (HIFU) for surgery.

Figure 1:
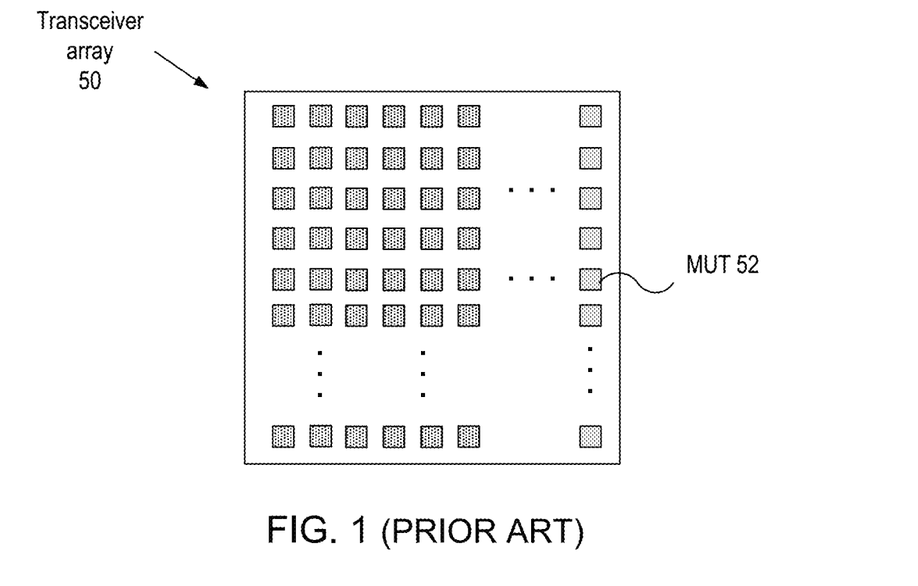
FIG. 1 shows a two dimensional rectilinear transceiver array in a conventional system.

Advances in micro-machining technologies allow sensors and actuators to be efficiently incorporated on a substrate. In particular, micromachined ultrasound transducers (MUTs), using capacitive transducers (cMUTs) or piezoelectric transducers (pMUTs), are particularly advantageous compared to the conventional MUTs having a large form factor. FIG. 1 shows a two dimensional rectilinear transceiver array 50 in a conventional system. As depicted, the transceiver array 50 may include: a set of MUTs 52 that generates and transmit pressure waves in a transmit mode/process and that receive pressure waves and develop electrical charge in response to the received pressure waves in a receive mode/process. As depicted, the MUTs 52 are uniformly spaced in the x- and y-directions, i.e., the distance from one MUT to a neighboring MUT along the x-direction (or the y-direction) is the same throughout the array. The MUTs 52 tend to have a limited number of vibrational resonances, i.e., the MUTs array 52 may have a limited bandwidth in the frequency domain. In general, the wider bandwidth the MUTs 52 have, the more sophisticated operational modes the MUTs 52 may be operated in and the better images the transceiver array 50 may be able to generate. As such, there is a strong need to design MUTs that have increased bandwidth for enhanced acoustic performances.

SUMMARY OF THE DISCLOSURE

In embodiments, a transducer array including a plurality of micromachined ultrasonic transducers (MUTs) arranged in an asymmetric arrangement.

In embodiments, an array of micromachined ultrasonic transducers (MUTs) includes MUTs arranged in a two dimensional array that has first and second rows, the MUTs in the first row being equally spaced by a horizontal pitch in a horizontal direction, the MUTs in the second row being equally spaced by the horizontal pitch in the horizontal direction. The MUTs in the second row are shifted along the horizontal direction by a first horizontal distance relative to the MUTs in the first row and shifted along a vertical direction by a first vertical distance relative to the MUTs in the first row. The first horizontal distance is greater than zero and less than the horizontal pitch. The first vertical distance ranges from one tenth of a horizontal width of a MUT of the plurality of MUTs to a half of a vertical height of the MUT.

In embodiments, an imaging system includes a transceiver tile for generating a pressure wave and converting an external pressure wave into an electrical signal, and a control unit for controlling the transceiver tile. The transceiver tile includes an array of micromachined ultrasonic transducers (MUTs), where the array includes MUTs arranged in a two dimensional array that has first and second rows, the MUTs in the first row being equally spaced by a horizontal pitch in a horizontal direction, the MUTs in the second row being equally spaced by the horizontal pitch in the horizontal direction. The MUTs in the second row are shifted along the horizontal direction by a first horizontal distance relative to the MUTs in the first row and shifted along a vertical direction by a first vertical distance relative to the MUTs in the first row. The first horizontal distance is greater than zero and less than the horizontal pitch. The first vertical distance ranges from one tenth of a horizontal width of a MUT of the plurality of MUTs to a half of a vertical height of the MUT.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, or a device.

Elements/components shown in diagrams are illustrative of exemplary embodiments of the disclosure and are meant to avoid obscuring the disclosure. Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

Figure 2:
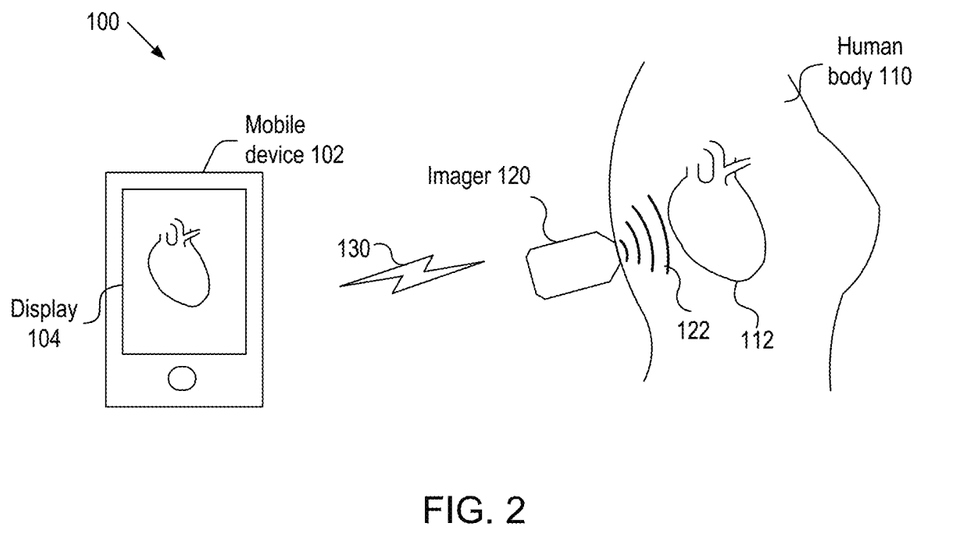
FIG. 2 shows an imaging system according to embodiments of the present disclosure.

FIG. 2 shows an imaging system 100 according to embodiments of the present disclosure. As depicted, the system 100 may include: an imager 120 that generates and transmit pressure waves 122 toward an internal organ 112, such as heart, in a transmit mode/process; and a device 102 that communicates signals to the imager through a communication channel 130. In embodiments, the internal organ 112 may reflect a portion of the pressure waves 122 toward the imager 120, and the imager 120 may capture the reflected pressure waves and generate electrical signals in a receive mode/process. The imager 120 may communicate the electrical signals to the device 102 and the device 102 may display images of the human organ on a display/screen 104 using the electrical signals.

It is noted that the imager 120 may be used to get an image of internal organs of an animal, too. It is also noted that the pressure wave 122 may be acoustic, ultrasonic, or photo-acoustic waves that can travel through the human/animal body and be reflected by the internal organs.

In embodiments, the imager 120 may be a portable device and communicate signals through the communication channel 130, either wirelessly or via a cable, with the device 102. In embodiments, the device 102 may be a mobile device, such as cell phone or iPad, or a stationary computing device that can display images to a user.

Figure 3:
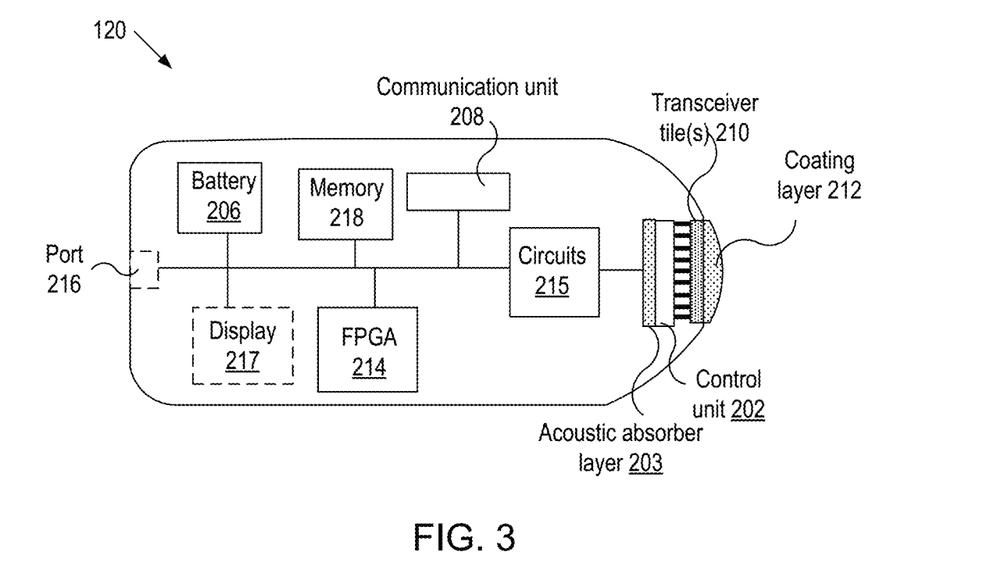
FIG. 3 shows a schematic diagram of an imager according to embodiments of the present disclosure.

FIG. 3 shows a schematic diagram of the imager 120 according to embodiments of the present disclosure. In embodiments, the imager 120 may be an ultrasonic imager. As depicted in FIG. 2, the imager 120 may include: a transceiver tile(s) 210 for transmitting and receiving pressure waves; a coating layer 212 that operates as a lens for focusing the pressure waves and also functions as an impedance interface between the transceiver tile and the human body 110; a control unit 202, such as ASIC chip, for controlling the transceiver tile(s) 210; a microprocessor 214 for controlling the components of the imager 120; a communication unit 208 for communicating data with an external device, such as the device 102, through one or more ports 230; a memory 218 for storing data; a battery 206 for providing electrical power to the components of the imager; and optionally a display 216 for displaying images of the target organs.

In embodiments, the device 102 may have a display/screen. In such a case, the display may not be included in the imager 120. In embodiments, the imager 120 may receive electrical power from the device 102 through one of the ports 230. In such a case, the imager 120 may not include the battery 206. It is noted that one or more of the components of the imager 120 may be combined into one integral electrical element. Likewise, each component of the imager 120 may be implemented in one or more electrical elements.

In embodiments, the user may apply gel on the coating layer 212 so that the impedance matching between the coating layer 212 and the human body 110 may be improved, i.e., the power loss at the interface is reduced.

Figure 4:
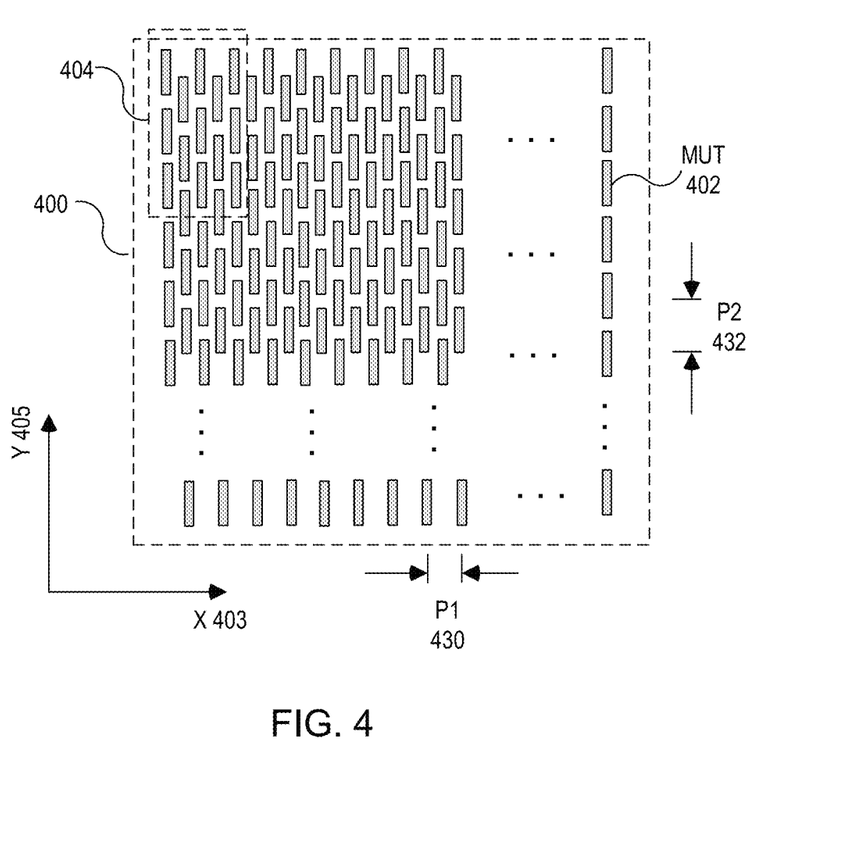
FIG. 4 shows an asymmetric (or staggered) rectilinear transceiver array according to embodiments of the present disclosure.

FIG. 4 shows an enlarged view of an asymmetric (or staggered) rectilinear transceiver array 400 including MUTs 402 according to embodiments of the present disclosure. In embodiments, the array 400 may be included in the transceiver tile 210. The MUTs 402 may be arranged in a staggered configuration to bring a benefit of the array acoustic performance. Hereinafter, the term staggered (or asymmetric) array refers to an array of MUTs, where the MUTs in a first row are shifted along the x-direction 403 relative to the MUTs in a second row. In embodiments, the MUTs in a row may be equally spaced by a horizontal distance (pitch) P1 430 and the MUTs in a column may be equally spaced by a vertical distance (pitch) P2 432.

In embodiments, each MUT 402 may by a pMUT and include a piezoelectric layer formed of at least one of PZT, KNN, PZT-N, PMN-Pt, AlN, Sc—AlN, ZnO, PVDF, and LiNiO$_3$. In alternative embodiments, each MUT 402 may be a cMUT. In FIG. 4, each MUT 402 is shown to have a rectangular shape. More specifically, each MUT may include a top electrode that has a rectangular projection area. It should be apparent to those of ordinary skill in the art that the top electrode may have other suitable geometrical shape, such as, square, circle, ellipse, oval, so on. For the purpose of illustration, in the drawings of the present application, each MUT is symbolically represented by the geometrical shape of the top electrode.

Figure 5:
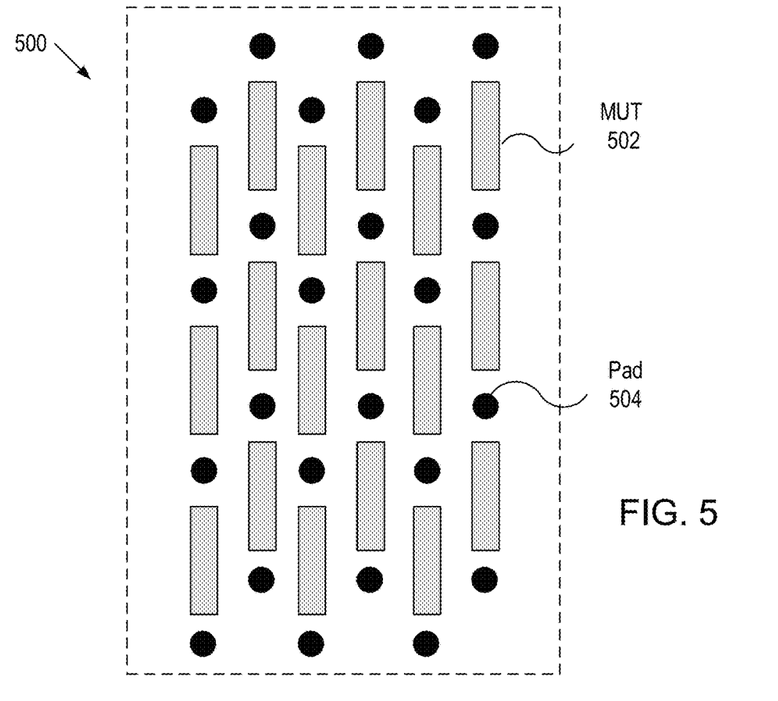
FIG. 5 shows an enlarged view of a MUT array according to embodiments of the present disclosure.

FIG. 5 shows an enlarged view of a MUT array 500 according to embodiments of the present disclosure. In embodiments, the array 500 may correspond to the portion of array 404 in FIG. 4. As depicted, the array 500 may include MUTs 502 and electrical pads 504. In embodiments, the MUTs 502 and pads 504 are arranged in a staggered configuration. In embodiments, each electrical pad 504 may electrically couple one or more of the MUTs 502 to a substrate, such as an ASIC or an electrical board (not shown in FIG. 5), where the substrate may contain electronics to send/receive electrical signals to/from the MUTs 502. In embodiments, the substrate may be disposed under the MUT array and each pad 504 may extend in a vertical direction (i.e., in a direction normal to the paper). It is noted that other electrical connections between the MUTs 502 and pads 504 are not shown in FIG. 5, but it should be apparent to those of ordinary skill in the art that suitable electrical connections, such as traces and wires, may be used to electrically connect the MUTs 502 to the pads 504.

Figure 6:
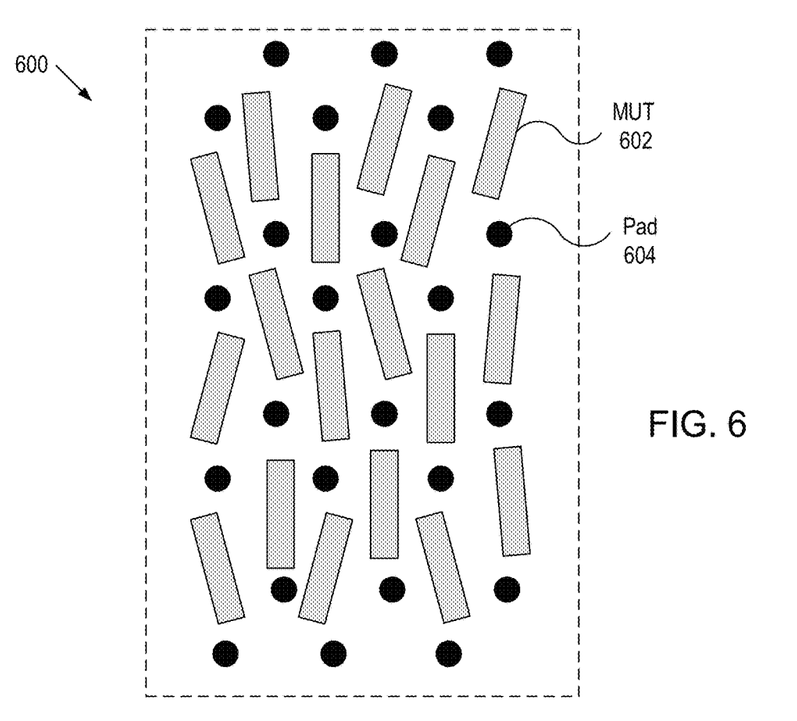
FIG. 6 shows an enlarged view of a MUT array according to embodiments of the present disclosure.

FIG. 6 shows an enlarged view of a MUT array 600 according to embodiments of the present disclosure. In embodiments, the array 600 may correspond to the portion of array 404 in FIG. 4. In embodiments, the MUTs 600 may be arranged in a staggered or asymmetric configuration and also certain amount of randomness may be introduced to the orientation of each MUT. In embodiments, the randomness may bring acoustic signal enhancement to an imager by reducing the crosstalk among MUTs 602. In embodiments, the randomly rotated MUT 602 may remain on the x-y plane, while each electrical pad 604 may be disposed in a comparable way to a pad location in the MUT array 500.

Figure 7:
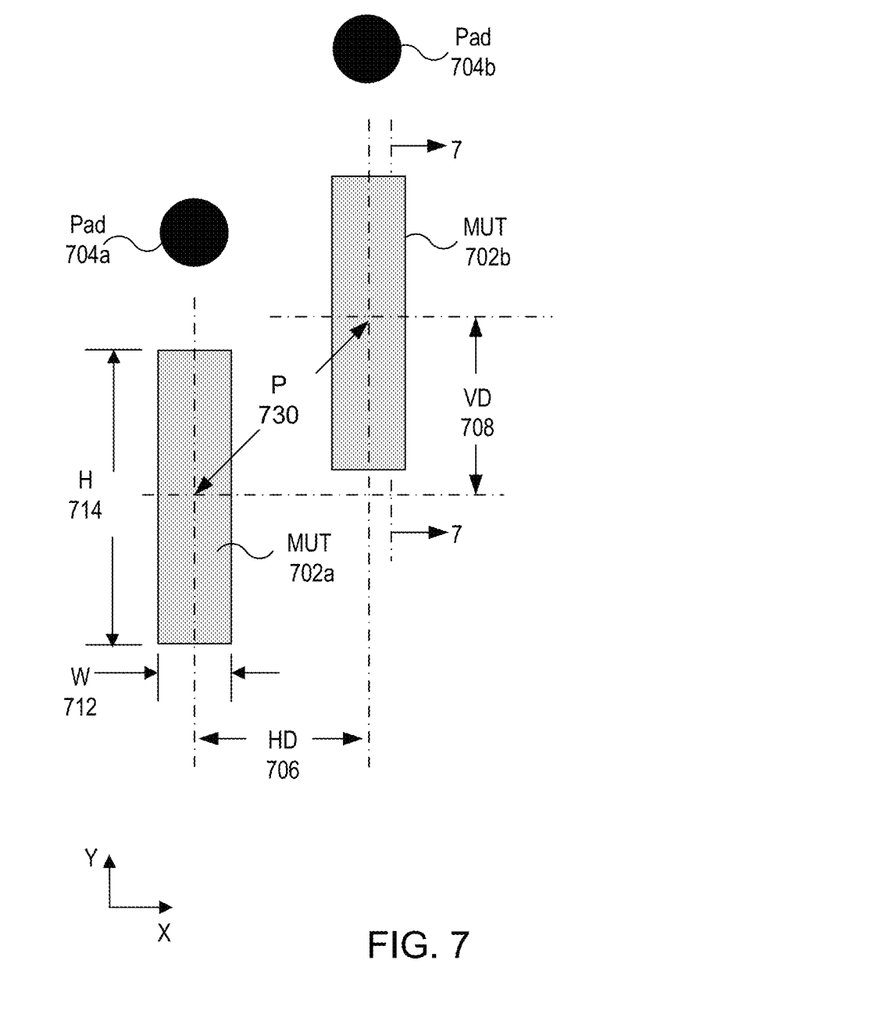
FIG. 7 shows two pairs of rectangular MUTs and pads that are arranged in a staggered configuration according to embodiments of the present disclosure.

FIG. 7 shows two pairs of MUTs 702 and pads 704 that are arranged in a staggered configuration according to embodiments of the present disclosure. For the purpose of illustration, each MUT is represented by a rectangle that is a projection area of the top electrode of the MUT. In embodiments, the two MUTs 702a and 702b in FIG. 7 may be two neighboring MUTs in the MUT array 400. As depicted, the MUTs 702a and 702b may be separated by a horizontal distance, HD, 706 in the x-direction and by a vertical distance, VD, 708 in the y-direction. Each MUT 702 may have a rectangular shape with the width, W, 712 and height, H, 714. In embodiments, the horizontal distance HD 706 may be greater than zero and less than four times the horizontal width 712 of the MUT and less than the pitch in the x-direction.

Unlike the conventional MUT array 50, in embodiments, the MUTs 702a and 702b may be arranged in a staggered configuration, i.e., the pair of MUT 702a and pad 704a in the first row may be shifted along the x-direction relative to the pair of MUT 702a and pad 704b in the second row. As a result of the staggered configuration, the MUT array 400 may have one or more asymmetric vibrational modes (or, shortly, asymmetric modes), resulting in a wider bandwidth than the conventional MUT array 50. As the MUT array 400 may have wider bandwidth, the MUT array may be operated in more sophisticated operational modes.

In general, the number density of the MUTs in a MUT array may affect the resolution of the images generated by the MUT array. In the conventional MUT array 50, the number density of the MUTs may be increased by decreasing the horizontal distance (or equivalently horizontal pitch) between the MUTs. However, in the conventional MUT array, the mutual impedance between two neighboring MUTs may also increase as the horizontal pitch decreases, which may negate the advantage obtained by the increase of number density. Hereinafter, the mutual impedance refers to the acoustic coupling between two MUTs. In contrast, in embodiments, the diagonal distance, P, 730 may be the effective separation between the MUTs 702a and 702b. As such, in embodiments, the mutual impedance may be less than the conventional symmetric MUT array that has the same horizontal separation HD 706. Stated differently, the staggering configuration may allow the number density to be increased without out increasing mutual impedance significantly.

Figure 8A:
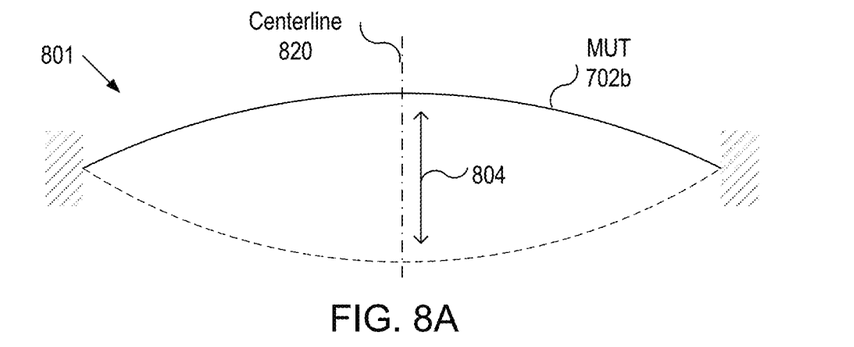
FIGS. 8A-8D show a set of vibrational mode shapes of a MUT, taken along a direction 7-7 in FIG. 7, according to embodiments of the present disclosure.
Figure 8B:
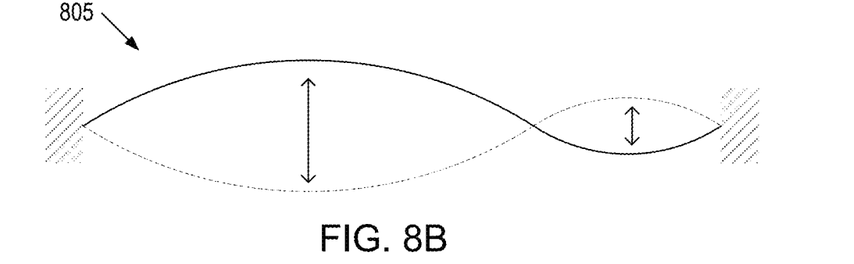
Figure 8C:
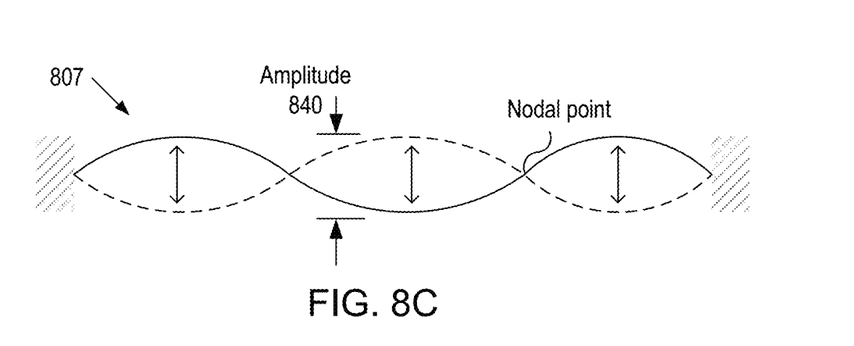
Figure 8D:
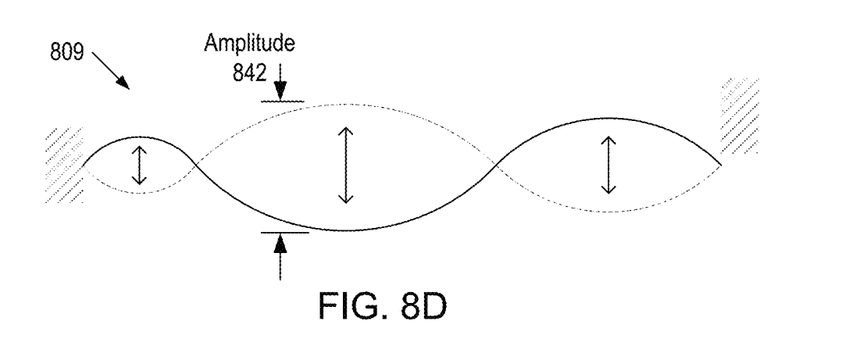
Figure 9:
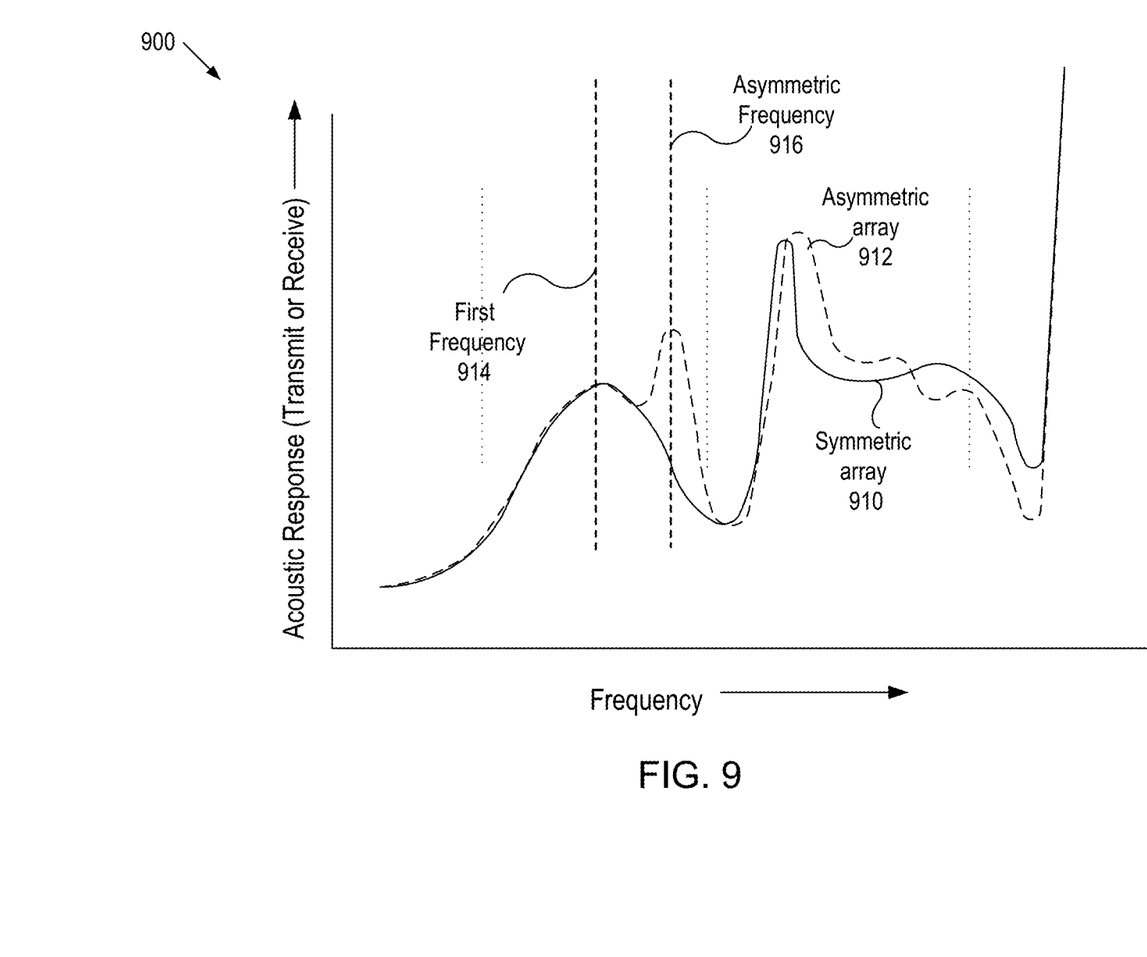
FIG. 9 shows a frequency response plot of an asymmetrical array according to embodiments of the present disclosure.

In embodiments, the vertical distance 708 may affect the characteristics of the asymmetric modes of vibration, such as the frequencies of the asymmetric modes and acoustic pressures at vibrational modes, as explained in conjunction with FIGS. 8A-9. Hereinafter, the term acoustic pressure refers to the level of acoustic power generated by each MUT. In embodiments, the vertical distance 708 may be preferably greater than one tenth of the width 712 and less than the half of the height 714. In embodiments, as the VD 708 increases up to less than one half of the height 714, an acoustic pressure amplitude at the asymmetrical modes may increase.

FIGS. 8A-8D show a set of vibrational mode shapes of the MUT 702b, taken along the direction 7-7 in FIG. 7, according to embodiments of the present disclosure. For the purpose of illustration, the MUT 702b is represented by a single line in FIGS. 8A-8D. However, it should be apparent to those of ordinary skill in the art that the MUT may include a stack of layers. As depicted, FIG. 8A and FIG. 8C present a first vibrational mode 801 and a third vibrational mode 807 of the MUT 702b at the first and third resonance frequencies, respectively, where an arrow 804 indicates the direction of motion of the MUT 702b. In embodiments, the first and third vibrational modes may be symmetric, i.e., each mode shape is symmetrical with respect to the centerline 820 of the MUT 720b. In embodiments, the symmetric modes may be generated even when the MUTs are not staggered, i.e., the symmetric MUT array 50 may have the symmetric vibrational modes in FIGS. 8A and 8C.

In embodiments, FIGS. 8B and 8D show the second vibrational mode 805 and fourth vibrational mode 809 at the second and fourth resonance frequencies of the MUT 702b, respectively. As depicted, the second and fourth vibrational modes may be asymmetric, i.e., the MUT is not symmetric with respect to the centerline 820. In embodiments, the asymmetry of the vibrational mode may be obtained by arranging the MUTs in the staggered (asymmetric) configuration, as shown in FIG. 4.

In general, the acoustic pressure performance, which refers to the energy of an acoustic pressure wave generated by each MUT at a frequency, may increase as the peak amplitude of the MUT increases at the frequency. In embodiments, an asymmetric mode may enable wider bandwidth than a symmetric mode when they are vibrating in the same order. For instance, the third mode 807 and fourth mode 809 may have the same order, i.e., the same number of nodal points, and the peak amplitude 840 of the third mode 807 is smaller than the peak amplitude 842 of the fourth mode 809.

FIG. 9 shows a frequency response plot 900 of the asymmetrical MUT array 400 according to embodiments of the present disclosure. In FIG. 9, the curve 912 shows the response (y-axis) of the array 400 as a function of frequency, where the response refers to the peak amplitude of the pressure waves generated by the array during the transmit mode or the electrical charge developed during the receive mode. In FIG. 9, the curve 910 shows the response of a symmetric array 50 as a function of frequency.

As depicted, the staggered MUT array 400 may have a resonance vibrational mode near the frequency 914, where the frequency 914 may be also the resonance vibrational mode of the symmetric MUT array 50. In embodiments, the staggered MUT array 400 in FIG. 7 may have additional resonance frequency at the frequency 916, which is referred to as asymmetric resonance frequency. In embodiments, with both symmetrical and asymmetrical modes of vibration, as depicted in FIG. 9, the gain of acoustic response may increase, and the bandwidth may improve since the MUT array 400 may be operated at both the center symmetric frequency 914 and a high asymmetric frequency 916.

It is noted that the frequency response curve 912 may include the contribution from all of the MUTs in the array 400. Since each MUT in the staggered MUT array 400 may have the same frequency response characteristics, each MUT has the similar frequency response curve to the curve 912, i.e., the each MUT in the asymmetric array 400 may have resonance frequencies at both the center symmetric frequency 914 and an asymmetric frequency 916.

Figure 10:
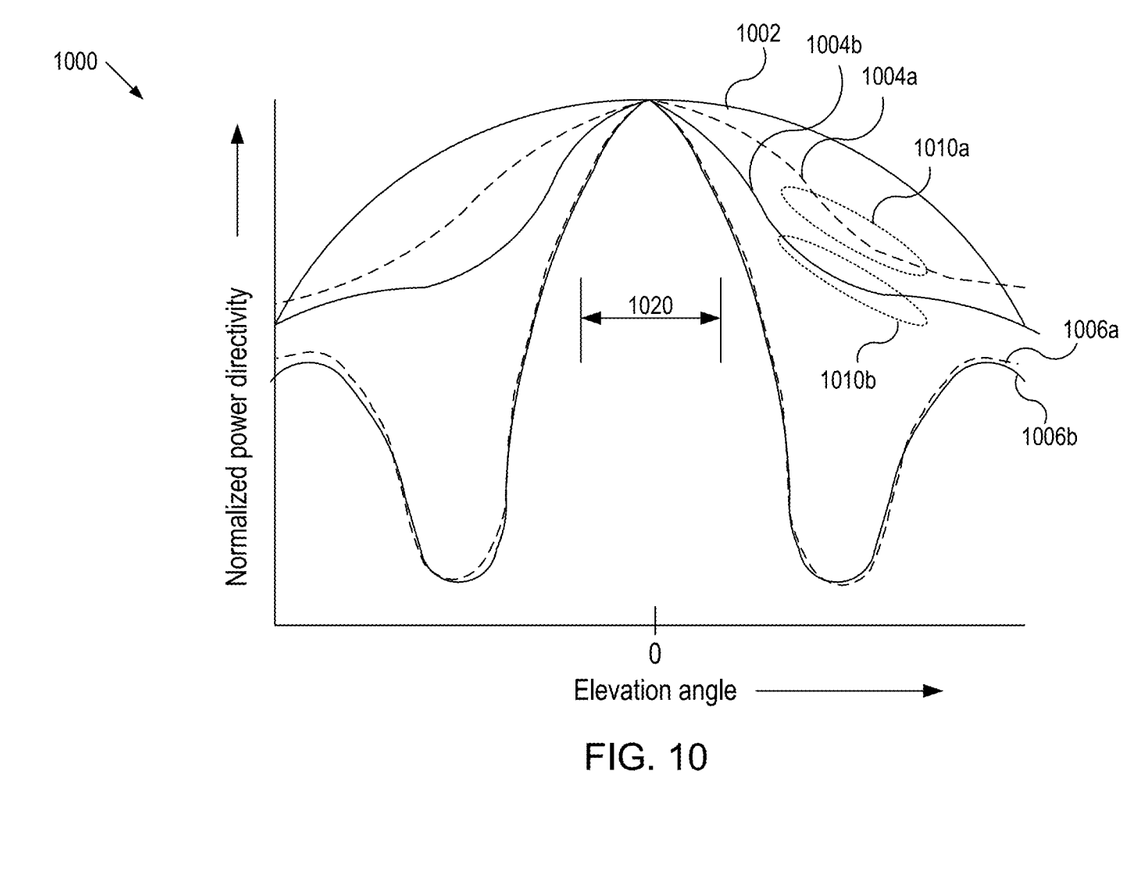
FIG. 10 shows a plot of acoustic beam pattern responses of MUT arrays as functions of elevation angle according to embodiments of the present disclosure.

In embodiments, a beamforming technique may be used to direct the pressure waves transmitted by the imager 120 to a particular angle, i.e., the pressure waves from the MUT array 400 may be combined in such a way that pressure waves at a particular angle (i.e., beamforming direction) experience constructive interference while others experience destructive interference. In embodiments, the control unit 202 may control the phase and/or amplitude of the pressure waves generated by the MUT array 400 to steer the beamforming direction. FIG. 10 shows a plot of acoustic beam pattern responses of MUT arrays as functions of elevation angle according to embodiments of the present disclosure. In FIG. 10, each curve shows the acoustic response (y-axis) of a MUT array as a function of elevation angle, where the acoustic response refers to the peak amplitude of the pressure waves generated by the MUT array during the transmit mode (or the electrical charge developed during the receive mode), and the elevation angle refers to the angular distance relative to the beamforming direction.

In general, the directivity, which refers to blocking of noise outside the direction of interest 1020, affects the signal-to-noise ratio in the beamforming. (Hereinafter, the term direction of interest refers to a preset angular range around the beamforming direction.) In FIG. 10, a curve 1002 may indicate a normalized power directivity for both an symmetric (staggered) MUT array (such as 400) and asymmetric (non-staggered) array (such as 50) at the frequency of 1.5 MHz. Curves 1006a and 1006b show the directivity of symmetric and asymmetric arrays, respectively, at the frequency of 3.0 MHz. As depicted, the symmetric MUT array may have similar beam patterns as the asymmetric MUT array at the frequencies of 1.5 MHz and 3.0 MHz.

Curves 1004a and 1004b show beam patterns of symmetric and asymmetric arrays, respectively, at the frequency of 5.7 MHz. As depicted, the asymmetric array has higher (improved) directivity than the symmetric array, resulting in improved signal-to-noise ratio and image quality. For instance, the curves 1004a and 1004b have regions 1010a and 1010b that are outside the direction of interest 1020. As the power level at the region 1010b is lower than the power level at the region 1010a, the asymmetric array may have improved signal-to-noise ratio, which in turn improves the image quality.

Figure 11:
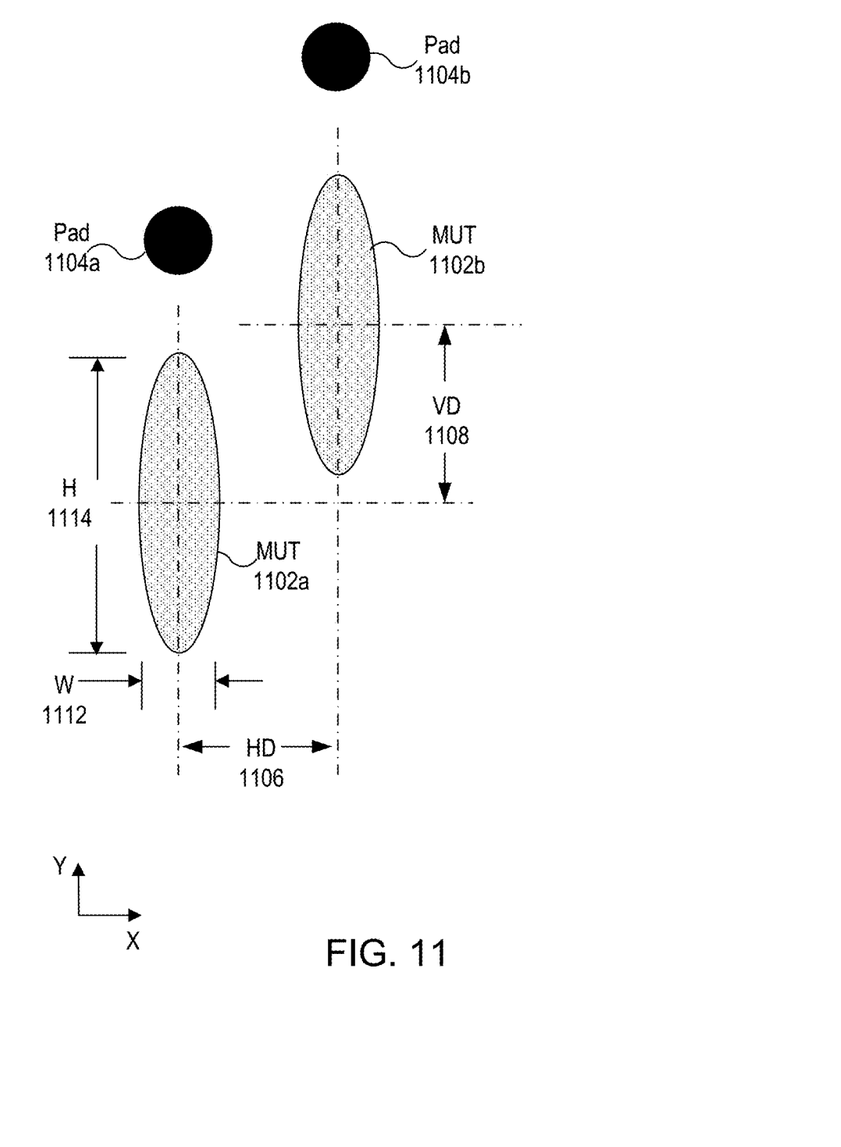
FIG. 11 shows two pairs of elliptical MUTs and pads that are arranged in a staggered configuration according to embodiments of the present disclosure.

In embodiments, the top electrodes of the MUTs in the array 400 may have different geometrical shapes, such as circle, ellipse, oval, so on. FIG. 11 shows two pairs of elliptical MUTs and circular pads that are arranged in a staggered configuration according to embodiments of the present disclosure. As depicted, the MUTs 1102 may be separated by a horizontal distance, HD, 1106 in the x-direction and by a vertical distance, VD, 1108 in the y-direction. Each MUT 1102 may have an elliptical shape with the width, W, 1112 and height, H, 1114.

Unlike the conventional MUT array 50, in embodiments, the MUTs 1102a and 1102b may be arranged in a staggered configuration, i.e., the pair of MUT 1102a and pad 1104a in the first row may be shifted along the x-direction relative to the pair of MUT 1104b and pad 1104b in the second row. In embodiments, the vertical distance 1108 may be preferably greater than one tenth of the horizontal width 1112 and less than one half of the vertical height 1114. In embodiments, as the VD 1108 increases up to one half of the vertical height 1114, an acoustic pressure amplitude at the asymmetrical modes may increase.

As a result of the staggered configuration, the MUT array having the staggered configuration in FIG. 11 may have the similar advantages as the MUT array having the staggered configuration in FIG. 7, i.e., the staggered MUT array in FIG. 11 may have improved bandwidth, image resolution, field of view, acoustic pressure, and mutual impedance between MUTs, compared to non-staggered MUT array. In embodiments, the MUTs may be separated by a horizontal distance 1106, where the horizontal distance 1106 may be greater than zero and less than four times the horizontal width 1112 of the MUT and less than the pitch in the x-direction.

Figure 12:
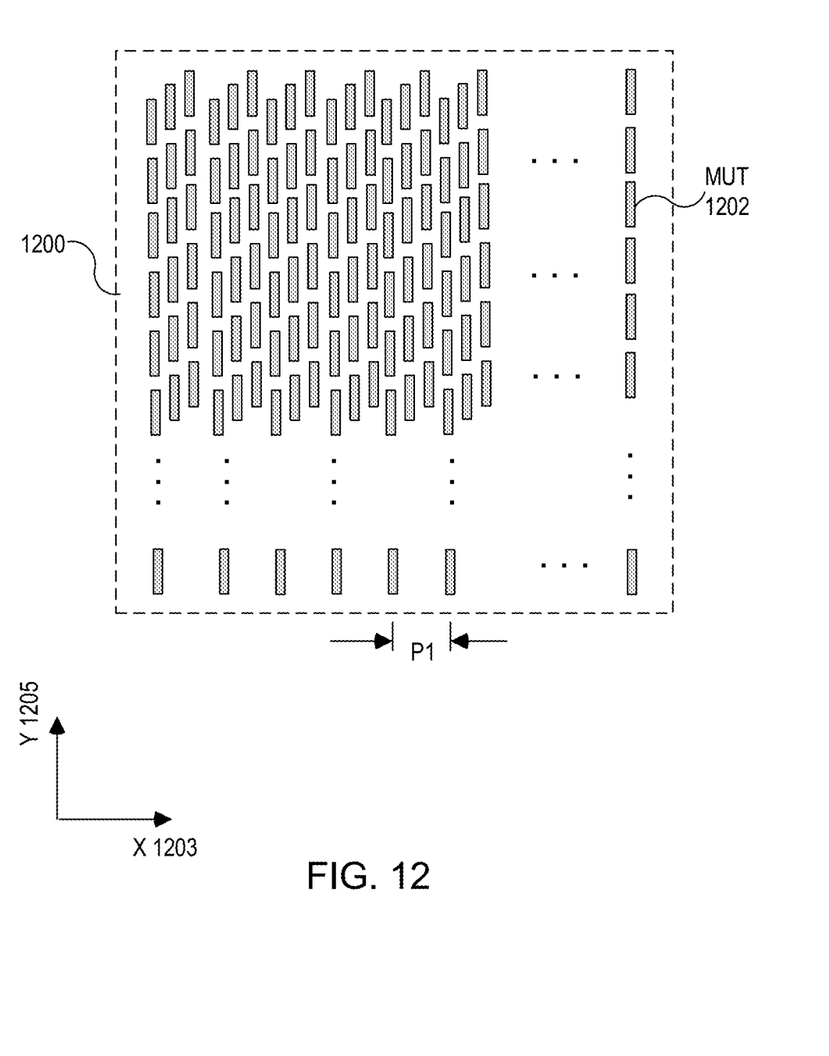
FIG. 12 shows an asymmetric (or staggered) rectilinear transceiver array according to embodiments of the present disclosure.

FIG. 12 shows an enlarged view of an asymmetric (or staggered) rectilinear transceiver array 1200 including MUTs 1202 according to embodiments of the present disclosure. The MUTs 1202 may be arranged in a staggered configuration to bring a benefit of the array acoustic performance. As depicted, the MUTs in each row may be equally spaced by a horizontal distance (pitch) and MUTs in each column may be equally spaced by a vertical distance (pitch). In embodiments, the MUTs in the second row may be shifted along the x-direction 1203 relative to the MUTs in the first row by a first horizontal distance, and the MUTs in the third row may be shifted along the x-direction relative to the MUTs in the first row by a second horizontal distance, where the first and second horizontal distances may be greater than zero and less than the horizontal pitch, P1.

Figure 13A:
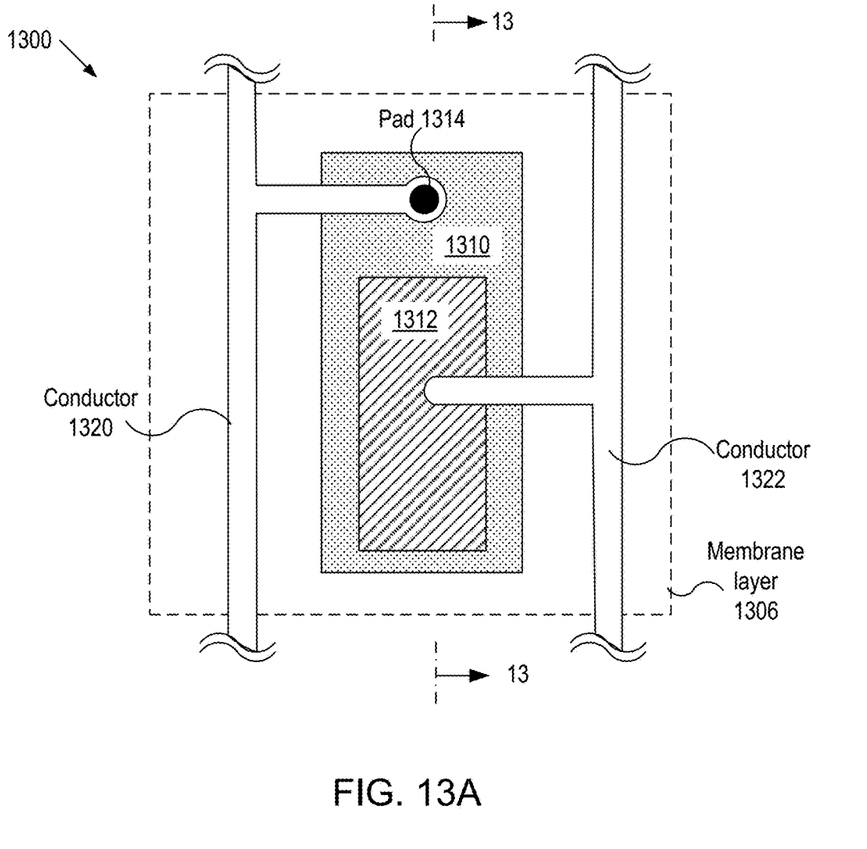
FIGS. 13A and 13B show top and cross-sectional views of an exemplary MUT according to embodiments of the present disclosure.
Figure 13B:
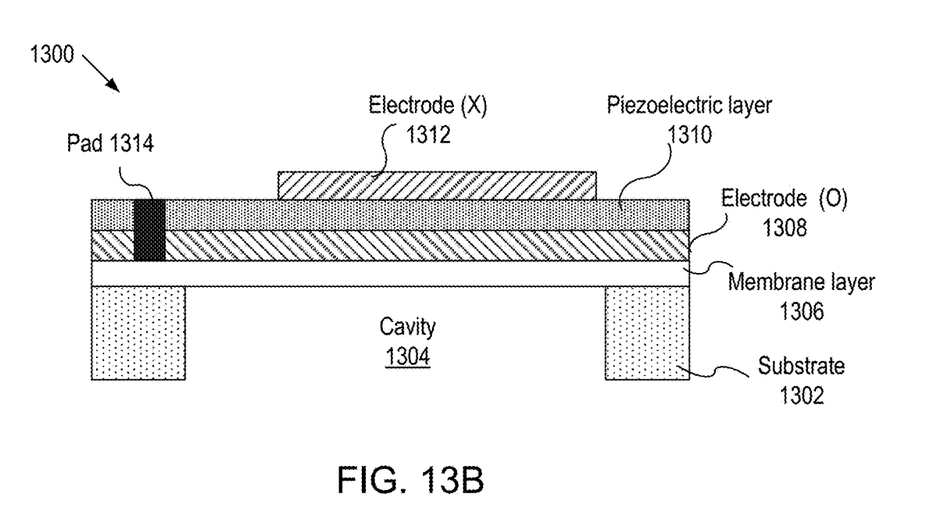

FIG. 13A shows a top view of an exemplary MUT 1300 according to embodiments of the present disclosure. FIG. 13B shows a cross-sectional view of the MUT 1300 in FIG. 13A, taken along the line 13-13, according to embodiments of the present disclosure. As depicted, the MUT may include: a membrane layer 1306, suspended from a substrate 1302; a bottom electrode (O) 1308 disposed on the membrane layer (or, shortly membrane) 1306; a piezoelectric layer 1310 disposed on the bottom electrode (O) 1308; and a top electrode (X) 1312 disposed on the piezoelectric layer 1310. In embodiments, an electrical pad 1314, which may be a via filled with electrically conducting material, may be formed so that the bottom electrode (O) 1308 may be electrically connected to an electrical conductor 1320. In embodiments, an electrical conductor 1322 may be electrically connected to the top electrode 1312. In embodiments, the electrical conductors 1320 and 1322 may be electrical wires or traces formed by patterning a metal layer. In embodiments, the pad 1314 and top electrode 1312 may correspond to the pad 704 (or 1104) and MUT 1102 (or 1102), respectively.

In embodiments, the substrate 1302 and the membrane 1306 may be one monolithic body and the cavity 1304 may be formed to define the membrane 1306. In embodiments, the cavity 1304 may be filled with a gas at a predetermined pressure or an acoustic damping material to control the vibration of the membrane 1306.

It is noted that the MUTs in the transceiver arrays 400 and 1200 may have other configuration than the MUT 1300 in FIG. 13A. For instance, each MUT may have more than one top electrode. It should be apparent to those of ordinary skill in the art that each rectangle (or ellipse) in FIGS. 4-7 (or FIGS. 11-12) symbolically represents a MUT, where the MUT may have one or more top electrodes and the top electrodes may have suitable geometrical shapes, such as circle, rectangle, ellipse, so on.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A transducer array, comprising:
   a plurality of micromachined ultrasonic transducers (MUTs) in an asymmetric arrangement, wherein each MUT of the plurality of MUTs has a dimension along a first direction that is larger than a dimension along a second direction and wherein the plurality of MUTs has a wider bandwidth than an other plurality of MUTs and wherein each MUT of the other plurality of MUTs has a same dimension along the first and second directions.

2. The transducer array of claim 1, wherein a center to center distance between the plurality of MUTs in one direction is different from a center to center distance between the plurality of MUTs in another direction.

3. The transducer array of claim 1, wherein the plurality of MUTs has a smaller mutual impedance than a plurality of MUTs in a symmetric arrangement.

4. The transducer array of claim 1, wherein the plurality of MUTs has one or more additional vibrational modes, compared to a plurality of MUTs in a symmetric arrangement.

5. The transducer array of claim 1, wherein each MUT of the plurality of MUTs has an elongated shape that supports one or more modes of vibration in a flexural mode of operation.

6. The transducer array as in one of claims 1-5, wherein the plurality of MUTs includes a group of elongated MUTs along an axis and the group of elongated MUTs are combined with a similar group of MUTs offset with each other in one direction.

7. The transducer array as in one of claims 1-5, wherein a projection area of each of the plurality of MUTs has a shape of rectangle, ellipse, or circle.

8. The transducer array as in one of claims 1-5, wherein sidelobe amplitudes of a beam generated by the plurality of MUTs are lower than sidelobe amplitudes of a beam generated by a plurality of MUTs in a symmetric arrangement.

9. The transducer array as in one of claims 1-5, wherein a bandwidth of the plurality of MUTs is wider than a bandwidth of a plurality of MUTs in a symmetric arrangement.

10. The transducer array as in one of claims 1-5, wherein each MUT of the plurality of the MUTs is rotated by a random angle with respect to an axial direction.

11. The transducer array of claim 1, wherein each of the plurality of MUTs performs at least one of transmitting an ultrasonic wave and receiving an ultrasonic wave.

12. The transducer array of claim 1, wherein each of the plurality of MUTs operates in at least one of symmetric vibrational mode and asymmetric vibration mode.

13. A transducer array, comprising:
a plurality of micromachined ultrasonic transducers (MUTs) in an asymmetric arrangement,
wherein the plurality of MUTs has a first effective grating angle without encountering grating lobes and wherein a plurality of MUTs in a symmetric arrangement has a second effective grating angle without encountering grating lobes and wherein the first effective grating angle is larger than the second effective grating angle.

14. The transducer array of claim 13, wherein a dimension of a MUT in one direction is larger than a dimension of the MUT in another direction.

15. The transducer array of claim 13, wherein a center to center distance between the plurality of MUTs in one direction is different from a center to center distance between the plurality of MUTs in another direction.

16. The transducer array of claim 13, wherein the plurality of MUTs has a smaller mutual impedance than a plurality of MUTs in a symmetric arrangement.

17. The transducer array of claim 13, wherein the plurality of MUTs has one or more additional vibrational modes, compared to a plurality of MUTs in a symmetric arrangement.

18. The transducer array of claim 13, wherein each MUT of the plurality of MUTs has an elongated shape that supports one or more modes of vibration in a flexural mode of operation.

19. The transducer array as in one of claims 14-18, wherein the plurality of MUTs includes a group of elongated MUTs along an axis and the group of elongated MUTs are combined with a similar group of MUTs offset with each other in one direction.

20. The transducer array as in one of claims 14-18, wherein a projection area of each of the plurality of MUTs has a shape of rectangle, ellipse, or circle.

21. The transducer array as in one of claims 14-18, wherein sidelobe amplitudes of a beam generated by the plurality of MUTs are lower than sidelobe amplitudes of a beam generated by a plurality of MUTs in a symmetric arrangement.

22. The transducer array as in one of claims 14-18, wherein a bandwidth of the plurality of MUTs is wider than a bandwidth of a plurality of MUTs in a symmetric arrangement.

23. The transducer array as in one of claims 14-18, wherein each MUT of the plurality of the MUTs is rotated by a random angle with respect to an axial direction.

24. The transducer array of claim 13, wherein each of the plurality of MUTs performs at least one of transmitting an ultrasonic wave and receiving an ultrasonic wave.

25. The transducer array of claim 13, wherein each of the plurality of MUTs operates in at least one of symmetric vibrational mode and asymmetric vibration mode.

* * * * *